(12) United States Patent
Chung et al.

(10) Patent No.: US 10,138,513 B2
(45) Date of Patent: Nov. 27, 2018

(54) METHOD AND DEVICE FOR AMPLIFYING AND DETECTING GENE USING GRAPHENE HEATER

(71) Applicant: Electronics and Telecommunications Research Institute, Daejeon (KR)

(72) Inventors: Kwang Hyo Chung, Daejeon (KR); Jin Tae Kim, Daejeon (KR); Yo Han Choi, Daejeon (KR); Choon Gi Choi, Daejeon (KR); Hong Kyw Choi, Daejeon (KR); Young Jun Yu, Daejeon (KR); Doo Hyeb Youn, Daejeon (KR); Jin Sik Choi, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 396 days.

(21) Appl. No.: 14/554,863

(22) Filed: Nov. 26, 2014

(65) Prior Publication Data
US 2016/0060681 A1    Mar. 3, 2016

(30) Foreign Application Priority Data

Aug. 29, 2014 (KR) ........................ 10-2014-0114013

(51) Int. Cl.
| | | |
|---|---|---|
| *B01L 7/00* | (2006.01) | |
| *H05B 3/14* | (2006.01) | |
| *H05B 3/42* | (2006.01) | |
| *C12Q 1/686* | (2018.01) | |
| *G01N 21/64* | (2006.01) | |

(52) U.S. Cl.
CPC ................ *C12Q 1/686* (2013.01); *B01L 7/52* (2013.01); *G01N 21/6486* (2013.01); *H05B 3/145* (2013.01); *H05B 3/42* (2013.01); *B01L 2200/12* (2013.01); *B01L 2300/0654* (2013.01); *B01L 2300/0816* (2013.01); *B01L 2300/1827* (2013.01); *G01N 2201/0231* (2013.01); *H05B 2203/013* (2013.01); *H05B 2203/037* (2013.01)

(58) Field of Classification Search
None
See application file for complete search history.

(56) References Cited

U.S. PATENT DOCUMENTS

| | | |
|---|---|---|
| 7,081,226 B1 | 7/2006 | Wittwer et al. |
| 8,735,103 B2 | 5/2014 | Chung et al. |
| 2004/0180346 A1* | 9/2004 | Anderson ............ C12Q 1/6806 435/6.18 |
| 2008/0131956 A1 | 6/2008 | Chung et al. |
| 2010/0267127 A1 | 10/2010 | Chung et al. |
| 2014/0017444 A1 | 1/2014 | Shimizu et al. |
| 2014/0080133 A1* | 3/2014 | Chen ..................... C12Q 1/686 435/6.12 |

FOREIGN PATENT DOCUMENTS

KR    10-2013-0086893 A    8/2013

OTHER PUBLICATIONS

Zhang et al. Biotechnology Advances 2006; 24: 243-284.*
Taylor et al. Nucleic Acids Research 1997; 25: 3164-3168.*
Kang et al. Nano Letters 2011; 11: 5154-5158.*
Krishnan et al. Analytical Chemistry 2004; 76: 6254-6265. (Year: 2004).*
Kwang Hyo Chung et al., "A Polymerase Chain Reaction (PCR) Chip Adopting Transparent Graphene Heater", Materials Research Society Fall Meeting & Exhibit, Dec. 1, 2013.

* cited by examiner

*Primary Examiner* — Angela M. Bertagna
(74) *Attorney, Agent, or Firm* — Rabin & Berdo, P.C.

(57) ABSTRACT

Provided is a gene amplifying and detecting device. The gene amplifying and detecting device includes: a gene amplifying chip including a chamber formed therein; a reaction solution filled in the chamber and including a fluorescent material; a light source located at one side of the gene amplifying chip; a light detector located at the other side of the gene amplifying chip; and a graphene heater formed on an inner surface or outer surface of the gene amplifying chip so as to heat the reaction solution.

17 Claims, 4 Drawing Sheets

METHOD AND DEVICE FOR AMPLIFYING AND DETECTING GENE USING GRAPHENE HEATER

TECHNICAL FIELD

The present invention relates to a device capable of amplifying and detecting genes and a method thereof, and more particularly, to a device capable of amplifying and detecting genes using a graphene heater and a method thereof.

BACKGROUND ART

Generally, since a small number of targeted genes to be detected are included in a targeted sample for gene analysis, direct measurement thereof is not easy. Accordingly, in most experimental tests which detect genes, a gene amplifying process is performed to increase the number of specific targeted genes before the genes are measured.

A polymerase chain reaction (PCR) technique is a representative technique which amplifies genes. The PCR technique forms a reaction solution by mixing a template DNA including a specific base sequence in a sample with polymerases, a primer set, dNTP, magnesium chloride, a buffer, or the like, and the number of genes can be amplified while a temperature of the reaction solution is changed according to thermal-cycling. The thermal-cycling includes three temperature sections, such as a denaturation operation, an annealing operation, and an extension operation, which are sequentially performed. In the PCR technique, the number of genes of a specific base sequence included in a template can be exponentially amplified by chain reaction using polymerases.

Further, a fluorescent material can be used for detecting genes. When the fluorescent material is added into a reaction solution, a fluorescent signal is increased in proportion to the number of genes (i.e., concentration), and thus, the fluorescent signal can be detected to measure the number of genes (i.e., concentration) which is amplified by the PCR.

Meanwhile, recently, PCR chips applied by various methods using micro-chips have been developed to perform a PCR process of amplifying genes at a super high speed and low cost. Further, various heating methods which perform thermal-cycling have been proposed. However, the conventional method has problems such as high power consumption, high manufacturing cost, etc.

In the case of a method in which an external heat source, such as a metal block, a film heater, or the like, contacts an outside of a PCR chip, relatively, heat response is slow, power consumption is high, manufacturing cost is high, and it is difficult to make a small size. Further, since the metal block or film heater cannot secure transparency, an optical path used for measuring a fluorescent signal should be specially designed.

In the case of a method in which a micro-patterned heater is directly installed on a surface of a PCR chip, heat response is fast, power consumption is low, and it is easy to make a small size. However, manufacturing cost is high, and an optical path cannot be secured due to opacity.

Further, in the case of a non-contact heating method using optical irradiation, it is difficult to make a small size because a device for the optical irradiation should be provided separately, and an adsorption material for heating should be included in a reaction solution.

As described above, since the conventional PCR chip includes a heating material for thermal-cycling, there are some problems such as heat response, power consumption, manufacturing cost, miniaturization, securement of an opacity for measuring fluorescence, etc.

DISCLOSURE

Technical Problem

The present invention is directed to providing a device which performs thermal-cycling to amplify genes using a graphene heater and detects the genes through an optical path which is transmitted through the graphene heater and a reaction solution, and a method thereof.

Technical Solution

One aspect of the present invention provides a gene amplifying and detecting device which includes: a gene amplifying chip including a chamber formed therein; a reaction solution filled in the chamber and including a fluorescent material; a light source located at one side of the gene amplifying chip; a light detector located at the other side of the gene amplifying chip; and a graphene heater formed on an inner surface or outer surface of the gene amplifying chip so as to heat the reaction solution.

Another aspect of the present invention provides a method of amplifying and detecting a gene which includes: filling a reaction solution including a fluorescent material in a chamber formed in a gene amplifying chip; heating the reaction solution using a graphene heater formed on an inner or outer surface of the gene amplifying chip and performing thermal-cycling of the reaction solution; supplying incident light from a light source located at one side of the gene amplifying chip; detecting emitted light by a light detector when the incident light is transmitted through the graphene heater and the reaction solution, and the transmitted light is adsorbed into the fluorescent material included in the reaction solution, and the adsorbed light excites the fluorescent material to emit the emitted light; and measuring an amount of amplified gene products from the detected emitted light.

Advantageous Effects

According to the embodiment of the present invention, thermal-cycling is performed to amplify genes by heating a reaction solution capable of amplifying genes included in a micro-chip using a transparent graphene layer installed on an outer or inner surface of the micro-chip for amplifying genes as a heater. Further, the genes are detected by measuring fluorescence using an optical path which is transmitted through the graphene heater and the reaction solution. Thus, since the thermal-cycling is performed using the graphene heater, power consumption can be decreased, manufacturing cost can be reduced, and it can make a smaller size. Further, since the graphene heater having high transparency is installed on a gene amplifying chip formed of a transparent material, the degree of freedom for an optical path design is increased and it is useful for making a small-sized device.

MODES OF THE INVENTION

Figure 1A:
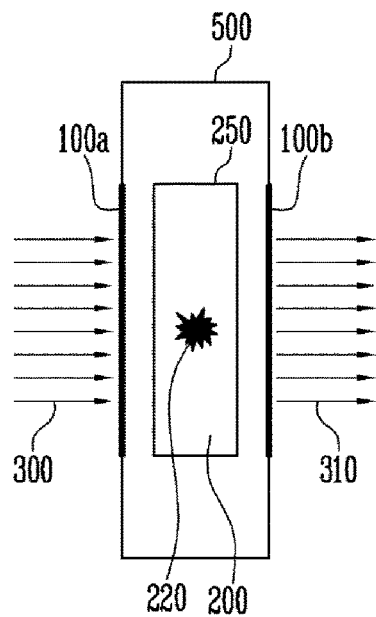
FIGS. 1A and 1B are cross-sectional views illustrating a structure of a gene amplifying/detecting device according to an embodiment of the present invention.

Hereinafter, exemplary embodiments of the present invention will be described in detail with reference to the accompanying drawings. In the drawings, the lengths and thicknesses of layers and regions may be exaggerated for clarity. In detailed descriptions of the exemplary embodiments of the present invention, detailed descriptions of well-known configurations unrelated to the gist of the present invention will be omitted. In this specification, when reference numerals are assigned to components of each drawing, it should be noted that, although the same components are illustrated in different drawings, the same numerals are assigned as much as possible.

Figure 1B:
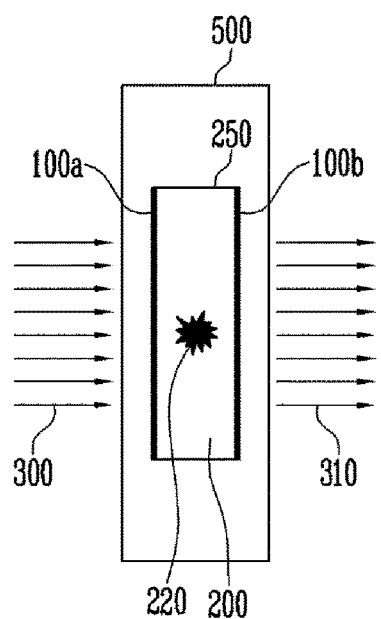

FIGS. 1A and 1B are cross-sectional views illustrating a structure of a gene amplifying/detecting device according to an embodiment of the present invention.

Referring to FIGS. 1A and 1B, the gene amplifying/detecting device includes a gene amplifying chip 500 and graphene heaters 100a and 100b. Genes included in a sample in the gene amplifying chip 500 are amplified by the graphene heaters 100a and 100b. Further, an amount of gene products amplified by an emitted light 310 may be quantitatively measured after an incident light 300 passes through the gene amplifying chip 500 and the graphene heaters 100a and 100b.

The gene amplifying chip 500 amplifies the genes included in the sample, and the genes may be amplified using a polymerase chain reaction (PCR) method. To this end, a chamber 250 is formed in the gene amplifying chip 500, and the chamber 250 is filled by a reaction solution 200 including a fluorescent material 220. The chamber 250 may be a micro-chamber. The reaction solution 200 may include a reaction solution capable of amplifying genes and a reaction solution capable of preprocessing the genes included in the sample for purification and enrichment. Further, the fluorescent material 220 uses a material in which intensity of luminescence increases in proportion to the number of genes. Thus, the number of amplified genes may be measured.

As the graphene heaters 100a and 100b heat the reaction solution 200 to perform thermal-cycling of PCR, the graphene heaters 100a and 100b may heat by receiving an external power source, and may generate a constant heat flux to the reaction solution 200. Therefore, temperature change is applied to the reaction solution 200 to amplify genes, and thus, the thermal-cycling is performed to amplify the genes. The gene amplifying chip 500 may include the plurality of graphene heaters 100a and 100b, and each of the graphene heaters 100a and 100b may heat at a different temperature. Accordingly, three temperature sections for the PCR, i.e., a denaturation section, an annealing section, and an extension section, may be implemented using the graphene heaters 100a and 100b.

Here, the graphene heaters 100a and 100b may be formed in a single layer graphene, a multilayer graphene, or a combination thereof. For example, the graphene heaters 100a and 100b may be formed by transferring a single layer or multilayer graphene formed by a chemical vapor deposition process, which is generally performed on thin film such as a copper film, a nickel film, or a copper-nickel alloy film, to the gene amplifying chip 500. A graphene layer formed by the chemical vapor deposition process has high transmittance, high conductivity, and flexibility, and thus, the graphene layer is suitable for the graphene heaters 100a and 100b. Further, the graphene layer formed by the chemical vapor deposition process may form the graphene heaters 100a and 100b using a roll-to-roll transferring process, a micro-nano patterning technique, etc. Accordingly, a process of mass production with low cost is possible and the gene amplifying chip 500 may be manufactured with low cost. Meanwhile, the graphene heaters 100a and 100b may be formed using reduced graphene oxide in order to use the process of mass production with low cost.

In order to perform thermal-cycling to amplify genes, the graphene heaters 100a and 100b may be installed at various locations in the gene amplifying chip 500 as needed. For example, the graphene heaters 100a and 100b may be located at both sides of the reaction solution 200 located therebetween. Referring to FIG. 1A, the graphene heaters 100a and 100b may be located on a surface of the gene amplifying chip 500, and formed at a location corresponding to the chamber 250 in which the reaction solution 200 is filled. Further, referring to FIG. 1B, the graphene heaters 100a and 100b may be located in the gene amplifying chip 500, and formed to be in contact with the chamber 250. For example, since the graphene heaters 100a and 100b are installed on an inner side surface of the chamber 250, the reaction solution 200 directly contacts the graphene heaters 100a and 100b, and thus, the reaction solution 200 may be heated. For reference, the graphene heaters 100a and 100b may be patterned with various shapes as requirements for heat flux uniformity, etc. Further, in another embodiment, although not shown in the drawings, the graphene heaters 100a and 100b may be installed on only one side of the reaction solution 200, and not installed on the other side of the reaction solution 200. Further, a cooling module, such as a fan, a fin, or a thermoelement, may be installed on the other side of the reaction solution 200 on which the graphene heaters 100a and 100b are not installed.

According to the above structure, incident light 300 is transmitted through one side of the gene amplifying chip 500, and is transmitted through the graphene heater 100a and the reaction solution 200. Here, the emitted incident light 300 is adsorbed into and excites the fluorescent material 220 included in the reaction solution 200, and the emitted light 310 is transmitted through the reaction solution 200 and the graphene heater 100b to be transmitted to the other side of the gene amplifying chip 500. Accordingly, the gene amplifying chip 500 may be formed of a transparent material, such as silver, glass, plastic, etc., so as that the incident light 300 and the emitted light 310 are easily transmitted without attenuation. Further, the graphene heaters 100a and 100b may be formed of a material have high transmittance, for example, transmittance of 80% or more. Further, the graphene heaters 100a and 100b may be formed by mixing materials having high transmittance, for example, materials having a transmittance of 80% or more, such as a metal thin film, a nano-material, etc., or by stacking the materials and a graphene layer.

Graphene is a carbon allotrope in which carbon atoms are arranged in an alveolate form in a two-dimensional view. As the graphene is a material having high conductivity, transparency, thermal conductivity, mechanical stiffness, etc., electrical, optical, and mechanical material properties are very unique and excellent, and thus, the graphene is suitable for various applications. Specifically, in a visible light region, approximately 97% of transparency may be secured in a single graphene layer, and a level in a range of 80 to 90% of transparency may be secured in a multilayer graphene. When heaters 100a and 100b are formed of the graphene having the high transparency, an optical path in which a fluorescent signal of amplified gene products passes through the graphene heaters 100a and 100b may be implemented. Further, since the graphene has a fast thermal response, the graphene heaters 100a and 100b having low power consumption may be implemented. Furthermore, since the graphene heaters 100a and 100b may not need an additional control device, the gene amplifying/detecting device may be formed in a small size.

Meanwhile, although not shown in the drawings, a temperature sensor may be additionally installed in the chamber 250 to monitor thermal-cycling. For example, the temperature sensor is installed at a location which is out of the paths of the incident light 300 and the emitted light 310. Further, a temperature control device may be additionally installed at an outside of the gene amplifying/detecting device to control a power supply into the graphene heaters 100a and 100b through the temperature sensor. Further, when the graphene heaters 100a and 100b require cooling, a cooling module, e.g., a fan, may be additionally installed.

Additionally, an additional process may be performed on surfaces of the graphene heaters 100a and 100b to form protective layers for improving conductivity and thermal uniformity. For example, a functional chemical group is attached on a graphene layer using a chemical doping method, thereby improving electron mobility. Further, conductivity is improved by additionally coating a metal material, such as gold, silver, copper, iron in a shape of nano-particles, nano-pillars, or a nano-thin film, on the graphene heaters 100a and 100b, and thermal uniformity may be improved in a large area. In another example, the protection layers of the graphene heaters 100a and 100b may be formed by coating a glass material, an insulating material, or the like on the graphene heaters 100a and 100b.

Figure 2:
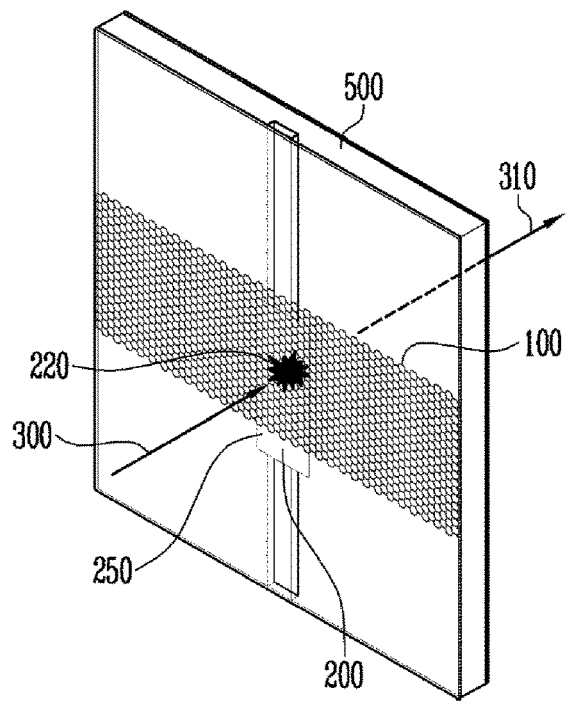
FIG. 2 is a three-dimensional view of a gene amplifying/detecting device according to an embodiment of the present invention.

FIG. 2 is a three-dimensional view of a gene amplifying/detecting device according to an embodiment of the present invention. Referring to FIG. 2, a gene amplifying chip 500 is formed in a plate shape, graphene heaters 100a and 100b are formed on both side surfaces of the gene amplifying chip 500. Here, a chamber 250 is formed to extend in a vertical direction, and the graphene heater 100 may overlap the chamber 250 and be formed to extend in a horizontal direction.

Figure 3:
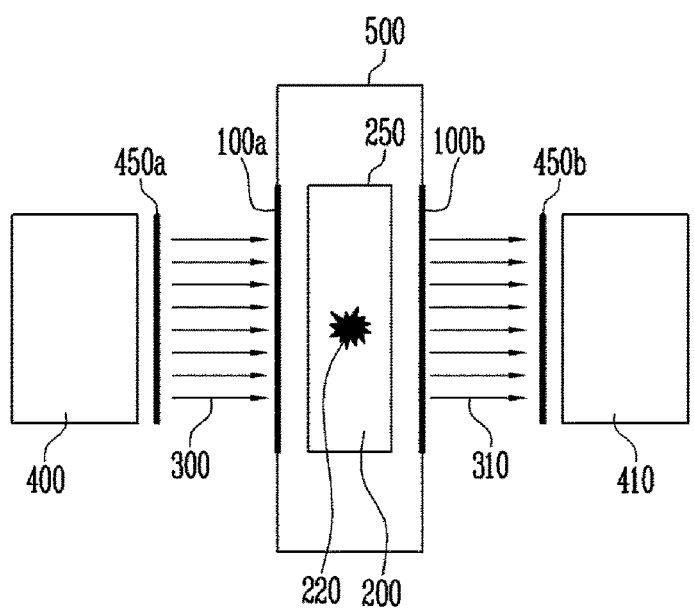
FIG. 3 is a cross-sectional view for describing a structure of a gene amplifying/detecting device according to an embodiment of the present invention and a method of measuring fluorescence of amplified gene products.

FIG. 3 is a cross-sectional view for describing a structure of a gene amplifying/detecting device according to an embodiment of the present invention and a method of measuring fluorescence of amplified gene products.

Referring to FIG. 3, a light source 400 is located at one side of a gene amplifying chip 500, and a light detector 410 is located at the other side of the gene amplifying chip 500. According to such a structure, an incident light 300 generated from the light source 400 is transmitted through a graphene heater 100a, a chamber 250, and a reaction solution 200. Further, an emitted light 310 is transmitted through the reaction solution 200, the chamber 250, and a graphene heater 100b, and then the emitted light 310 is detected by the light detector 410. As a result, a path of the light is formed. According to such a transmission-type optical path, the light source 400 and the light detector 410 may be separated spatially. Accordingly, arrangement of optical modules is easy and a loss of a light signal may be minimized.

The incident light 300 is adsorbed into a fluorescent material 220 included in the reaction solution 200 and an excitation light is emitted. Further, since the light detector 410 measures light intensity of the emitted light 310, an amount of amplified gene products may be quantitatively detected.

Further, light filters 450a and 450b may be additionally installed in an optical path to efficiently perform adsorbing light into the fluorescent material 220 and detecting the light by the light detector 410. For example, the light filters 450a and 450b are installed between the light source 400 and the gene amplifying chip 500 and between the light detector 410 and the gene amplifying chip 500, respectively.

Figure 4A:
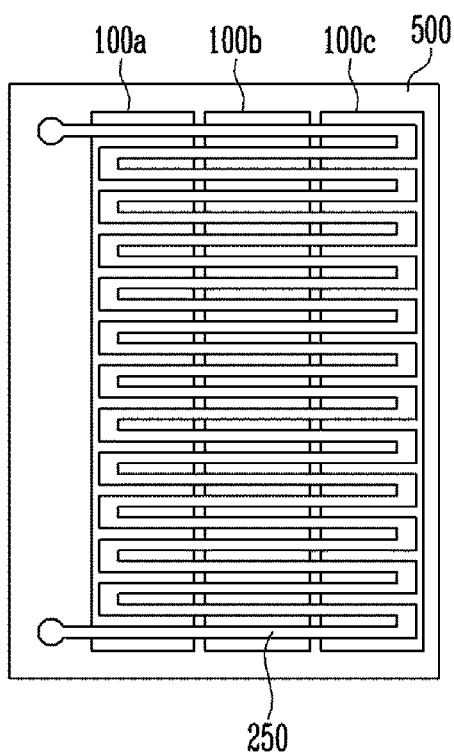
FIGS. 4A to 4C are plan views illustrating various application examples of a gene amplifying chip 500 according to an embodiment of the present invention.
Figure 4B:
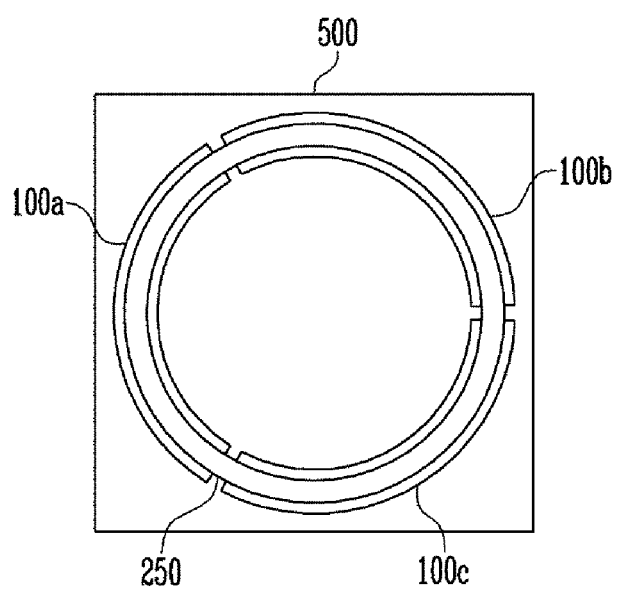
Figure 4C:
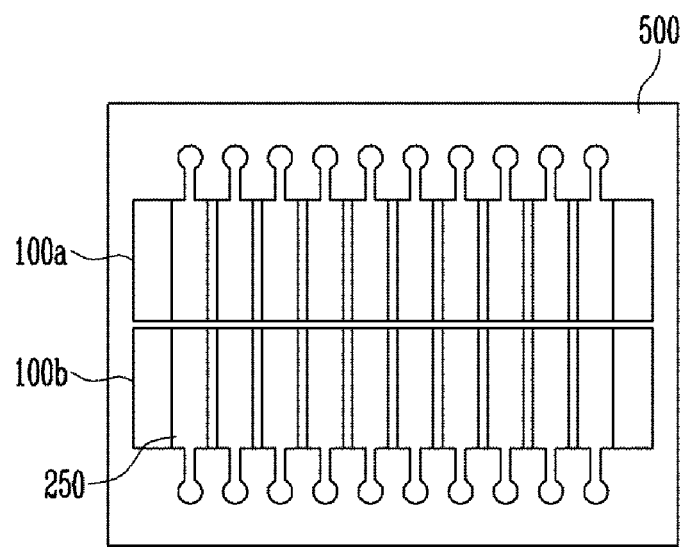

FIGS. 4A to 4C are plan views illustrating various application examples of a gene amplifying chip 500 according to an embodiment of the present invention. In general, the gene amplifying chip 500 may be divided into a static gene amplifying method which performs thermal-cycling in a state in which the reaction solution 200 is spatially stopped, and a dynamic gene amplifying method which performs thermal-cycling by moving the reaction solution 200. There is a micro-chamber type as an example of the static method, and a continuous flow type and a convection type as examples of the dynamic method. The gene amplifying chip 500 using graphene heaters 110a to 110c of the embodiment of the present invention may modify a micro-chamber 250 and the graphene heaters 100a, 100b, and 100c to various shapes in order to implement the static or dynamic gene amplifying method.

FIG. 4A is an example of a gene amplifying chip as a continuous flow type. As described in the drawing, a chamber 250 is bent in a serpentine shape, and a reaction solution 200 may continuously flow along the chamber 250. The graphene heaters 110a to 110c are located to overlap the chamber 250.

FIG. 4B is an example of a gene amplifying chip as a convection type. As described in the drawing, a chamber 250 is in a ring shape, and a reaction solution 200 may convect along the chamber 250. The graphene heaters 110a to 110c may be formed to surround the chamber 250 formed in a ring shape.

FIG. 4C is an example of a gene amplifying chip as a micro-chamber type. As described in the drawing, a gene amplifying chip 500 includes a plurality of micro-chambers 250, one of graphene heaters 100a and 100b may be formed to overlap the plurality of micro-chambers 250. In this case, since one of the graphene heaters 100a and 100b may heat the plurality of micro-chambers 250 at the same time, the number of amplified genes may be further increased.

In the drawings and specification, there have been disclosed typical exemplary embodiments of the invention, and although specific terms are employed, they are used in a generic and descriptive sense only and not for purposes of limitation. In addition, it will be understood by those of ordinary skill in the art that various changes in form and details may be made therein without departing from the spirit and scope of the present invention.

The invention claimed is:
1. A gene amplifying and detecting device, comprising:
 a gene amplifying chip including a chamber formed therein, the gene amplifying chip having a first sidewall and a second sidewall opposite to the first sidewall;
 a reaction solution in the chamber and including a fluorescent material;

a light source adjacent to the first sidewall of the gene amplifying chip;

a light detector located adjacent to the second sidewall of the gene amplifying chip; and a first graphene heater adjacent to the first sidewall of the gene amplifying chip so as to heat the reaction solution to cause a circulating flow of the reaction solution by convection, wherein the first graphene heater is positioned between the light source and the chamber to transmit light generated from the light source into the chamber.

2. The device of claim 1, wherein the first graphene heater is in contact with the first sidewall of the gene amplifying chip.

3. The device of claim 1, wherein the first graphene heater is formed in the gene amplifying chip to be in contact with the chamber.

4. The device of claim 1, wherein the first graphene heater is formed of a single layer graphene or a multilayer graphene having a transmittance of 80% or more.

5. The device of claim 1, further comprising a second graphene heater adjacent to the second sidewall of the gene amplifying chip.

6. The gene amplifying and detecting device of claim 5, wherein:

the second graphene heater is configured to heat at a different temperature from a temperature at which the first graphene heater is configured to heat.

7. The gene amplifying and detecting device of claim 5, wherein:

the first graphene heater and the second graphene heater are configured to implement a plurality of heating sections respectively for denaturation and annealing.

8. The gene amplifying and detecting device of claim 5, wherein the second graphene heater is in contact with the chamber or the second sidewall of the gene amplifying chip.

9. The device of claim 5, wherein the second graphene heater is positioned between the chamber and the light detector, the transmitted light is adsorbed into the fluorescent material included in the reaction solution, the adsorbed light excites and is emitted from the fluorescent material, and the emitted light is detected by the light detector through the second graphene heater.

10. The device of claim 1, wherein the fluorescent material emits light in proportion to a number of genes included in the reaction solution, and an amount of amplified gene products is measured through an intensity of emitted light measured by the light detector.

11. The device of claim 1, wherein the gene amplifying chip is formed of a transparent material.

12. The device of claim 1, wherein the reaction solution includes one of a first reaction solution for gene amplification and a second reaction solution for gene preprocessing for purification and enrichment of genes in a sample.

13. The device of claim 1, further comprising a first light filter located between the light source and the gene amplifying chip and a second light filter located between the light detector and the gene amplifying chip.

14. The device of claim 1, further comprising a temperature sensor formed in the gene amplifying chip and configured to sense a temperature of the reaction solution.

15. The device of claim 1, further comprising a protection layer formed on the graphene heater and including a chemical doping material, a metal material, a glass material, graphene oxide, or a nanostructure.

16. The gene amplifying and detecting device of claim 1, wherein:

the first graphene heater has a first width and the chamber has a second width parallel to the first width, and the first width is greater than the second width.

17. The gene amplifying and detecting device of claim 1, wherein the chamber is in a ring shape.

* * * * *